United States Patent [19]

Bartley et al.

[11] 4,446,251

[45] May 1, 1984

[54] PROCESS FOR PRODUCING TWO-CARBON ATOM OXYGENATED COMPOUNDS FROM SYNTHESIS GAS WITH MINIMAL PRODUCTION OF METHANE

[75] Inventors: William J. Bartley; Thomas P. Wilson, both of Charleston, W. Va.

[73] Assignee: Union Carbide Corporation, Danbury, Conn.

[21] Appl. No.: 358,897

[22] Filed: Mar. 17, 1982

Related U.S. Application Data

[63] Continuation-in-part of Ser. No. 121,985, Feb. 15, 1980, abandoned, which is a continuation-in-part of Ser. No. 52,869, Jun. 28, 1979, abandoned.

[51] Int. Cl.$^3$ .............................................. C07C 27/06
[52] U.S. Cl. ................................. 518/716; 518/714; 518/721; 518/717
[58] Field of Search ............................................ 518/716

[56] References Cited

U.S. PATENT DOCUMENTS

| | | | |
|---|---|---|---|
| 4,014,913 | 3/1977 | Ellgen et al. | 260/449 R |
| 4,096,164 | 6/1978 | Ellgen et al. | 260/449 R |
| 4,101,450 | 7/1978 | Hwang et al. | 252/460 |
| 4,116,994 | 9/1978 | Vannice et al. | 260/449 R |
| 4,210,597 | 7/1980 | Huang | 260/449 R |
| 4,224,236 | 9/1980 | Wunder et al. | 260/449 R |
| 4,235,798 | 11/1980 | Bartley et al. | 260/449 R |

FOREIGN PATENT DOCUMENTS

| | | |
|---|---|---|
| 21241 | 1/1981 | European Pat. Off. . |
| 1501892 | 2/1978 | United Kingdom . |

OTHER PUBLICATIONS

Bhasin et al., J. of Catalysis, 54, 120–128 (1978).

*Primary Examiner*—Howard T. Mars
*Attorney, Agent, or Firm*—Bernard Francis Crowe

[57] ABSTRACT

A process for selectively preparing a mixture of two-carbon atom oxygenated hydrocarbons, namely, acetic acid, ethanol and acetaldehyde, by continuously contacting a gaseous reaction mixture containing hydrogen and carbon monoxide with a solid catalyst comprising rhodium in combination with sodium at reaction conditions correlated so as to favor the formation of a substantial proportion of such two-carbon atom products.

5 Claims, No Drawings

PROCESS FOR PRODUCING TWO-CARBON ATOM OXYGENATED COMPOUNDS FROM SYNTHESIS GAS WITH MINIMAL PRODUCTION OF METHANE

CROSS-REFERENCE TO RELATED APPLICATION

This application is a continuation of Ser. No. 121,985 filed Feb. 15, 1980 now abandoned which is a continuation-in-part of application Ser. No. 052,869, filed on June 28, 1979 now abandoned.

This application is related to U.S. application Ser. No. 052,841, filed on June 28, 1979, now U.S. Pat. No. 4,235,798 which describes a process for producing the aforementioned two-carbon atom compounds using a catalyst containing rhodium and an alkali metal selected from among lithium, potassium, cesium and rubidium.

BACKGROUND

This invention concerns an improvement in the selective preparation of two-carbon atom oxygenated hydrocarbons, namely acetic acid, ethanol, and/or acetaldehyde, from synthesis gas. More particularly, the invention concerns the reaction of synthesis gas in the presence of a rhodium-sodium catalyst under heterogeneous reaction conditions correlated to produce such two-carbon atom products.

The preparation of hydrocarbons and oxygenated hydrocarbons from synthesis gas (essentially a mixture of carbon monoxide and hydrogen) has received extensive study and has achieved commercial adoption. Reaction conditions generally involve temperatures on the order of 150°–450° C., pressures from atmospheric to about 10,000 psig, and hydrogen-to-carbon monoxide ratios in the range of 4:1 to about 1:4, with an iron group or a noble metal group hydrogenation catalyst.

One serious disability of most synthesis gas processes for the production of oxygenated hydrocarbons containing two or more carbon atoms has been the non-selective or non-specific nature of the product distribution. Catalysts which possess acceptable activity generally tend to give a wide spectrum of products, for example, hydrocarbons and oxygenated hydrocarbons having a broad distribution of carbon atom contents. This not only complicates the recovery of desired products, but results in the wastage of reactants to commercially uninteresting byproducts.

United Kingdom Pat. No. 1,501,892 is directed to a process for selectively preparing a mixture of two-carbon atom oxygenated compounds, namely, acetic acid, ethanol and acetaldehyde, using a rhodium catalyst. United Kingdom Pat. No. 1,501,891 describes a process for favoring the production of ethanol relative to acetic acid and acetaldehyde by incorporating iron into the rhodium-based catalyst. U.S. Pat. Nos. 4,096,164, 4,014,913 and copending application Ser. No. 841,054 filed Oct. 11, 1977, concern themselves with enhancing the productivity and/or varying the distribution of the aforementioned two-carbon atom oxygenated compounds by the addition of elements such as molybdenum and/or tungsten, manganese, and thorium and/or uranium, respectively, to the rhodium-based catalyst.

Rhodium catalysts supported by carriers containing sodium, among other materials, have been used for the production of oxygenated hydrocarbons from synthesis gas. In the aforementoned United Kingdom Pat. No. 1,501,892, Table V describes the various rhodium catalysts used in the experiments of the patent, several of which catalysts are shown to have been supported on Davison 59 silica gel. The chemical composition of such Grade 59 silica gel is provided in Grace Technical Bulletin IC-773-15 which indicates the presence of 0.10 weight % $Na_2O$ (corresponding to 0.074 wt. % Na) in the gel. A lower sodium value for gels or this type is disclosed in Grace Technical Bulletin 202 (1958) at page 2, where a sodium level of 0.02 weight % is indicated to be typical of Davison silica gels. In The Journal of Catalysis, Vol. 54, pp. 120–128 (1978), Bhasin et al. disclose synthesis gas reactions with rhodium catalysts supported on Davison Grace 59 silica gel. At page 121, Table 1 of this publication, the sodium content of the silica gel support is reported to be 0.085 weight %. Thus, the sodium content of silica gel supports of the type used in conjunction with the rhodium catalysts described in the aforementioned United Kingdom patent and the Bhasin et al disclosure is reported in the technical literature to be as low as 0.02 weight % and as high as 0.085 weight %.

An undesirable feature of the synthesis gas process disclosed in the aforementioned patents and The Journal of Catalysis publication is the production of methane along with the desired two-carbon atom oxygenated hydrocarbons. In general, the greater the efficiency of the reaction to methane, the lower the production of the desired oxygenated hydrocarbons. Since methane is a significantly less valuable commercial chemical than either ethanol, acetic acid or acetaldehyde, methane formation is economically undesirable. Moreover, inasmuch as carbon monoxide and hydrogen, the reactants in these processes, are generally produced commercially by steam reforming of methane, the formation of methane, in turn, from synthesis gas necessarily detracts from the overall process efficiency.

SUMMARY OF THE INVENTION

This invention describes a catalyst for the production of two-carbon atom oxygenated hydrocarbons from the reaction of carbon monoxide and hydrogen. The catalyst of the invention acts to inhibit methane formation and shift the distribution of two-carbon atom oxygenated hydrocarbons produced by the reaction in favor of acetic acid while retaining the selectivity of the overall reaction toward such two-carbon atom compounds. The process of the invention involves contacting a catalyst comprising rhodium in combination with sodium under suitable reaction conditions with synthesis gas to selectively produce acetic acid, ethanol and/or acetaldehyde, the concentration of sodium in the catalyst being at least 0.1 weight percent. The catalyst may optionally be combined with an alkali metal such as lithium, potassium, cesium or rubidium to inhibit methane formation as a coproduct among the desired oxygenated compounds. In a preferred embodiment of the invention, the catalyst additionally contains manganese to improve the rate of the reaction with regard to the formation of two-carbon atom products.

PROCESS DISCUSSION

The reaction is conducted at reaction conditions of temperature, pressure, gas composition and space velocity correlated so as to collectively produce acetic acid, ethanol, and/or acetaldehyde in an amount which is at least about 50 weight percent, preferably at least about 75 weight percent, of the two or more carbon atom compounds obtained by the reaction. Desirably, the reaction is conducted at these correlated conditions to achieve carbon efficiencies to the specified products based on carbon consumption in excess of 10%, and frequently in excess of 50%.

At optimum reaction conditions, and particularly at relatively low conversions, there is little conversion to three-carbon atom and higher hydrocarbons and oxygenated hydrocarbons, and conversion to methane and methanol may be minimized. The reaction efficiency, or selectivity to the two-carbon atom compound is at least about 10%, and is usually upwards of about 25%; under the preferred conditions it exceeds 50% and, under optimum conditions, can reach 90% or more. Selectivity is defined herein as the percentage of carbon atoms converted from carbon monoxide to a specified compound or compounds other than $CO_2$.

Thus, the independent reaction variables are correlated so as to favor the formation of a substantial proportion of the desired two-carbon atom oxygenated hydrocarbons (acetic acid, ethanol, and acetaldehyde). This proportion, expressed as carbon conversion efficiency, is usually greater than 25% and frequently exceeds 50%.

In one aspect of the invention, this correlation is a combination of conditions which result in maintaining moderate reaction conditions to thereby limit the conversion of CO to not more than about one-fourth, preferably not more than about one-eighth, such fractional conversion being expressed on a single pass basis. As will be discussed in detail below, this may be achieved primarily by a combination of high space velocity and low temperature, but other factors (e.g., $H_2/CO$ ratio, catalyst activity, pressure, bed geometry, etc.) also affect the conversion. At high conversions, it has been noted that hydrocarbons and higher carbon number oxygenated hydrocarbons are produced in excess, with a resulting loss in efficiency to two-carbon atom compounds.

Conditions of temperature, of pressure, and of gas composition are usually within the ranges that are essentially conventional for synthesis gas conversions, particularly those employed in the production of methanol. Thus, existing technology and, in some instances, existing equipment may be used to effect the reaction.

The reaction is highly exothermic, with both the thermodynamic equilibrium and the kinetic reaction rates being governed by the reaction temperature. Average catalyst bed temperatures are usually within the range of about 150°–450° C., but for optimum conversions, bed temperatures are kept within the range of about 200°–400° C., typically about 250°–350° C.

The reaction temperature is an important process variable, affecting not only total productivity but selectivity toward one or more of the desired two-carbon atom products. Over relatively narrow temperature ranges, as for example 10° to 20° C., an increase in temperature may somewhat increase total synthesis gas conversion, tending to increase the efficiency of ethanol production and decrease the efficiency of acetic acid and acetaldehyde production. At the same time, however, higher temperatures favor methane production, and apparently methane production increases much more rapidly at higher temperatures than do conversions to the more desirable two-carbon atom products. Thus, for a given catalyst and with all other variables held constant, the optimum temperature will depend more on product and process economics than on thermodynamic or kinetic considerations, with higher temperatures tending to increase the production of oxygenated products but disproportionately increasing the co-production of methane.

In the discussions above, the indicated temperatures are expressed as average, or mean, reaction bed temperatures. Because of the highly exothermic nature of the reaction, it is desirable that the temperature be controlled so as not to produce a runaway methanation, in which methane formation is increased with higher temperature, and the resulting exotherm increases the temperature further. To accomplish this, conventional temperature control techniques are utilized, as for example the use of fluidized bed reaction zones, the use of multistage fixed bed adiabatic reactors with inter-stage cooling, or relatively small catalyst particles placed in tube-and-shell type reactors with a coolant fluid surrounding the catalyst-filled tubes. In this regard, reference is made to U.S. Pat. No. 4,125,553, issued Nov. 14, 1978.

The reaction zone pressure is desirably within the range of about 15 psig and about 10,000 psig, economically within the range of about 300–5,000 psig. Higher reaction zone pressures increase the total weight of product obtained per unit time and likewise improve the selectivity toward two-carbon atom compounds.

The ratio of hydrogen to carbon monoxide in the synthesis gas may vary widely. Normally the mole ratio of hydrogen to carbon monoxide is within the range of 20:1 to 1:20, or preferably within the range of about 5:1 to about 1:5. However, in some instances, it may be advantageous to operate with a hydrogen to carbon monoxide mole ratio as low as about 1:200. In most of the experimental work reported herein, the mole ratio of the hydrogen to carbon monoxide is about 1:1. Increasing the ratio tends to increase the total rate of reaction, sometimes quite significantly, and has a smaller though favorable effect on the rate of production of two-carbon atom products, but concurrently increases selectivity to methane. Increasing the hydrogen to carbon monoxide ratio also favors the formation of more highly reduced products, that is, ethanol rather than acetaldehyde or acetic acid. Carbon dioxide, which may be present in a typical case in an amount of up to about 10 mole percent in the synthesis gas, has essentially no effect.

One of the features of the present invention is the recognition that a low conversion, e.g., preferably less than 20% of the CO per pass, favors the formation or production of a substantial proportion of acetic acid, ethanol, and/or acetaldehyde, generally in excess of 10%. This conversion is conveniently achieved by employing a high space velocity correlated with other reaction variables (e.g., temperature, pressure, gas composition and catalyst). Space velocities in excess of about $10^3$ gas hourly space velocity (volumes of reactant gas, at 0° C. and 760 mm mercury pressure, per volume of catalyst per hour, commonly referred to as "GHSV") are generally employed, although it is preferable that the space velocity be within the range of about $10^4$ to about $10^6$ per hour. Excessively high space velocities result in uneconomically low conversions, while excessively low space velocities cause the production of more diverse spectrum of reaction products, including higher boiling hydrocarbons and oxygenated hydrocarbons.

The rhodium-sodium catalyst of the invention comprises rhodium provided in combination with sodium upon a support material. This is typically effected by depositing rhodium and sodium onto a particular support material and placing the supported combination into the reaction zone. For purposes of the invention, the catalyst composition may advantageously include other elements, such as an alkali metal selected from among lithium, potassium cesium and rubidium; iron, manganese and molybdenum/tungsten, the use of which in conjunction with rhodium are disclosed, respectively, in copending applications Ser. No. 052,841, filed on June 28, 1979 herewith, Ser. No. 676,129, filed Apr. 12, 1976, U.S. Pat. No. 4,014,913 and U.S. Pat. No. 4,096,164.

On the basis of experience to date, the amount of catalyst on the support should range from about 0.01 weight percent to about 25 weight percent, based on the combined weight of the metal catalyst and the support material. Preferably, the amount of catalyst is within the range of about 0.1 to about 10 weight percent.

The mole ratio of sodium to rhodium in the catalyst should generally vary from about 0.01 to 10, preferably from about 0.1 to 5 to effect a reduction in the methane carbon efficiency in accordance with the invention. Most preferably, the sodium/rhodium mole ratio should be within the range of about 0.2 to 1.

A relatively high surface area particulate support, e.g., one having a surface area upwards of about 1.0 square meters per gram (BET low temperature nitrogen adsorption isotherm method) is preferred, desirably upwards of about 10 square meters per gram, although surface area alone is not the sole determinative variable. Based on research to date, silica gel is preferred as the catalyst base or support, with graphite, graphitized carbon, alpha alumina, manganese oxides, magnesia, eta-alumina, gamma-alumina, and active carbon being less desirable.

For the purpose of this invention, it is believed that rhodium deposited on either particles of sodium oxide or a carrier containing sodium is substantially the same as rhodium and sodium codeposited on any of the above support materials.

The rhodium and sodium may be deposited onto the catalyst base or support by any of the techniques commonly used for catalyst preparation, as for example, impregnation from an organic or inorganic solution, precipitation, coprecipitation, or cation exchange. Conveniently, a solution of a heat decomposable inorganic or organic rhodium compound and a sodium compound is appropriately contacted with the support material, and the support then dried and heated, the latter advantageously under reducing conditions, to form the finely dispersed sodium-containing rhodium catalyst. Any of these materials may be deposited concurrently or sequentially. It suffices for the present to say that inorganic or organic compounds or rhodium and sodium are appropriately contacted with the support material, and the support then dried and heated, the latter advantageously under reducing conditions, to form the finely dispersed rhodium and sodium.

The rhodium deposited is typically in metal form, desirably as fine discrete particles. The form of the sodium component is, however, not completely appreciated. It may be chemically associated with the rhodium or it may be in a physical admixture with the rhodium. For example, the sodium may be alloyed with the rhodium or not, in the form of a metal or an oxidized state of the metal, or it may be in the form of an oxide, a silicate, a carbonate, or the like.

DESCRIPTION OF TEST REACTOR

The reactor used in these studies was a 316 stainless steel, bottom-agitated "Magnedrive" autoclave of the J. M. Berty design with a centrally positioned catalyst basket and a side product effluent line. it is of the type depicted in FIG. 1 of the paper by Berty, Hambrick, Malone and Ullock, entitled "Reactor For Vapor-Phase Catalytic Studies", presented as Preprint 42E at the Symposium on Advances in High-Pressure Technology—Part II, Sixty Fourth National Meeting of the American Institute of Chemical Engineers (AIChE), at New Orleans, Louisiana, on Mar. 16–20, 1969 and obtainable from AIChE at 345 East 47th. Street, New York, N.Y. 10017. A variable speed, magnetically driven fan continuously recirculated the reaction mixture over the catalyst bed. The following modifications were found to facilitate operation and inhibit run-away methanation reactions.

1. Hydrogen feed gas was introduced continuously at the bottom of the autoclave through the well for the shaft of the Magnedrive agitator.

2. Carbon monoxide feed gas was introduced continuously through a separate port at the bottom of the autoclave, in order to avoid a hydrogen-rich zone in the autoclave.

Effluent gases were removed through a port in the side of the reactor. Condensable liquid products were removed from the exit stream in a brine-cooled condenser at ca. 5° to 10° C. and were collected in a holding tank under pressure. The non-condensable components of the exit stream were vented through a wet test meter at atmospheric pressure to determine their total volume. A rubber septum in the atmospheric pressure line permitted syringe sampling of the non-condensable gases. No external recycle was employed.

DESCRIPTION OF THE TEST PROCEDURE

The bulk volume of the weighed catalyst sample was determined and the sample was placed in the catalyst basket. The quantity of catalyst charged varied from about 10 cc to about 100 cc. The quantity of catalyst to be charged was chosen to give an estimated reactant gas conversion of less than 10 percent. Gold-plated screens and thin layers of glass wool were placed above and below the catalyst bed to prevent circulation of solid fines. The catalyst basket was charged to the reactor, and the reactor then sealed. The sealed reactor and the process lines were pressure tested at ambient temperatures to a pressure about 500 to 1000 psig in excess of the maximum anticipated working pressure. Nitrogen, hydrogen, or a mixture of the two was used for this test.

When the reactor was shown to be leak free, pure hydrogen was passed through the reactor, and the temperature raised to about 240° C. The hydrogen and carbon monoxide flows were then adjusted at a mole ratio of 1:1 to give an approximate purge rate of 500 STP* liters/hr. This corresponds to a space velocity of from about 5000 to about 50,000 STP volumes of gas per volume of catalyst per hour depending upon the volume of catalyst charged in the particular example. The hydrogen-carbon monoxide ratio was determined by gas chromatographic analysis of an effluent gas aliquot.

*"STP" means standard temperature and pressure defined as 0° C. and 1 atm. pressure.

When the appropriate gas composition was obtained, the reactor temperature was raised to the value desired.

A period from about 0.5 hour to about one hour was allowed for the reactor to reach a steady-state at the new temperature. The liquid product trap was then drained, a wet test meter reading was taken, and the time was noted as the beginning of a run. During the course of a run, one or more effluent gas samples were analyzed for hydrogen, carbon monoxide, acetaldehyde, methane, and other volatile hydrocarbons. At the end of a run, the liquid product was collected, and the volume of effluent gas was noted. The liquid product was analyzed by gas chromatography.

Succeeding runs with the same catalyst were made either at the same conditions or at new conditions of temperature of feed gas flow rates. If any of the conditions were changed, approximately one hour was allowed for the reactor to come to a new steady-state before beginning a new run.

PREPARATION OF CATALYSTS

The catalysts cited in the examples below were all prepared by essentially the following sequence of steps: The desired quantities of rhodium trichloride or rhodium (III) nitrate, manganese (II) nitrate, and sodium nitrate, depending upon the desired catalyst composition, were dissolved in distilled water at ambient temperature. The volume of distilled water taken for the preparation of this solution was chosen to just fill the void volume (pores) of the support sample being impregnated. Davison TM Grade 59 silica gel (8–20 mesh-U.S. Sieves) was placed in a vacuum flask. The top of the flask was sealed with a rubber septum, and the flask was evacuated through the side arm. A syringe needle was then used to inject the solution onto the evacuated support. When addition was complete, the impregnated support was allowed to stand at one atmosphere for ca. 30 minutes. It was then carefully dried in a nitrogen atmosphere using the following sequence: 80° C. (for 1 hr.); 110° C. (2 hrs.); 150° C. (2 hrs.); and about 250° C. (2 hrs.). The dried, impregnated support was placed in a quartz tube through which hydrogen was continuously passed. The temperature was raised from 100° to 500° C., over a five to six hour period and then held at 500° C. for 1 one hour. The reduced catalyst was cooled to ambient temperature in an atmosphere of flowing nitrogen or hydrogen.

In order to remove significant amounts of impurities which were present in the support material as received from the manufacturer, the Davison TM Grade 59 silica support was initially "washed" with oxalic acid prior to being used as the catalyst support. Such treatment consisted of passing a mixture of oxalic acid, glycerine, and water in proportions of 1:1.5:2.5 by weight, respectively, through a bed of support material (length/diameter ratio of about 20 to 25) contained within a glass tube which drained through a stopcock at its base. The contents of the tube were maintained at about 90° C. by means of resistance heating wire wrapped around the exterior of the tube. About 2.5 volumes of oxalic acid solution were used to wash one volume of 8–20 mesh silica gel over a three-hour period. The material was then washed with about six volumes of distilled water at 90° C. over a period of about four hours and then dried at 350° C. for about four hours.

The chemical analysis of the silica gel for iron, aluminum, sodium and calcium impurities following the above-described treatment was as follows:

Iron as $Fe_2O_3$ 0.01 wt. % ±0.004%
Aluminum as $Al_2O_3$ 0.01 wt. % ±0.004%
Sodium as $Na_2O$ 0.01 wt.% ±0.004%
Calcium as CaO 0.02 wt. % ±0.01%

Table I which follows summarizes the data for a series of silica-gel supported rhodium catalysts containing manganese and sodium. The catalysts were tested at 300° C., 1000 psig total pressure, and a hydrogen to carbon monoxide mole ratio of about unity, according to the aforementioned test procedure in the above-described test reactor. Ethyl esters and acetates which were formed were included as ethanol and acetic acid in determining productivities and selectivities as used in the data presented herein. That is, in calculating ethanol and acetic acid values, credit was taken for quantities obtainable by hydrolyses of esters determined to be present.

The examples in the table illustrate the effect of sodium addition of rhodium catalysts, namely, a significant decrease in the carbon efficiency to methane and an increase in the acetic acid selectivity among the two-carbon atom oxygenated hydrocarbon products.

TABLE I

PERFORMANCE DATA[a] FOR 2.5 WEIGHT PERCENT SUPPORTED RHODIUM CATALYSTS CONTAINING VARYING LEVELS OF MANGANESE AND SODIUM

| Examples | Variables[b] % Mn | % Na | % Catalyst Volume | % Carbon Conv. | Carbon Efficiency, Percent[c] $CH_4$ | Gaseous HC | Total HC | Acetaldehyde | Ethanol | Acetic Acid | $C_2$ Compounds | Rate, lb/cf/hr Acetaldehyde | Ethanol | Acetic Acid | $C_2$ Compounds |
|---|---|---|---|---|---|---|---|---|---|---|---|---|---|---|---|
| A | 0.0 | 0.40 | 100. | 0.91 | 15.52 | 1.38 | 16.91 | 36.54 | 20.16 | 25.80 | 82.50 | 0.51 | 0.29 | 0.48 | 1.28 |
| B | 0.10 | 0.0 | 40. | 15.31 | 31.15 | 13.33 | 44.48 | 26.20 | 11.41 | 17.07 | 54.67 | 15.37 | 7.02 | 13.68 | 36.08 |
| C | 0.10 | 0.05 | 30. | 6.83 | 23.34 | 11.15 | 35.67 | 35.51 | 6.48 | 20.31 | 62.30 | 12.39 | 2.37 | 9.68 | 24.44 |
| D | 0.10 | 0.10 | 30. | 2.65 | 17.48 | 13.63 | 31.11 | 33.77 | 6.25 | 25.43 | 65.45 | 4.57 | 0.88 | 4.68 | 10.14 |
| E | 0.10 | 0.20 | 30. | 3.20 | 14.35 | 6.62 | 20.97 | 38.72 | 5.45 | 33.22 | 77.38 | 6.35 | 0.93 | 7.39 | 14.67 |
| F | 0.10 | 0.40 | 30. | 3.31 | 16.40 | 5.78 | 22.18 | 38.33 | 5.66 | 31.60 | 75.59 | 6.48 | 1.00 | 7.24 | 14.72 |
| G | 0.30 | 0.05 | 30. | 6.37 | 24.57 | 11.37 | 35.94 | 33.62 | 6.77 | 22.03 | 62.42 | 10.95 | 2.30 | 9.78 | 23.03 |
| H | 0.30 | 0.10 | 30. | 5.74 | 19.67 | 10.52 | 30.19 | 36.28 | 5.09 | 26.35 | 67.72 | 10.64 | 1.56 | 10.54 | 22.74 |
| I | 0.30 | 0.20 | 30. | 3.99 | 16.14 | 7.35 | 23.49 | 36.89 | 5.31 | 32.79 | 74.99 | 7.52 | 1.13 | 9.09 | 17.74 |

TABLE I-continued
PERFORMANCE DATA[a] FOR 2.5 WEIGHT PERCENT SUPPORTED RHODIUM CATALYSTS CONTAINING VARYING LEVELS OF MANGANESE AND SODIUM

| Ex- | Variables[b] | | Catalyst Volume | % Carbon Conv. | Carbon Efficiency, Percent[c] | | | | | | | Rate, lb/cf/hr | | | |
|---|---|---|---|---|---|---|---|---|---|---|---|---|---|---|---|
| am-ples | % Mn | % Na | | | $CH_4$ | Gaseous HC | Total HC | Acetal-dehyde | Eth-anol | Acetic Acid | $C_2$ Compounds | Acetal-dehyde | Eth-anol | Acetic Acid | $C_2$ Compounds |
| J | 0.30 | 0.40 | 30. | 2.08 | 16.25 | 6.31 | 22.56 | 35.94 | 6.81 | 33.66 | 76.41 | 3.83 | 0.76 | 4.83 | 9.42 |

[a] Catalysts were tested at 300° C. The partial pressures of carbon monoxide and hydrogen were each about 500 psi. Values are averages of from 4 to 10 data points. Estimated standard deviations are typically about 10 percent of the average value.
[b] Catalysts are supported on oxalic acid-washed Division ™ Grade Silica gel. % Mn, and % Na are the nominal weight percentages of manganese and sodium, respectively, which were deposited on the support in addition to 2.5 weight percent rhodium. "Catalyst Volume" is the number of cc of catalyst charged to the reactor; the nominal total gas feed to the catalyst was 22.3 gram moles per hour. "Carbon Conv." is the percent carbon conversion; i.e., the percentages of CO molecules fed which were converted to products other than $CO_2$.
[c] Percent carbon efficiency to a particular product is defined as 100 times the number of moles of carbon in that product divided by the number of moles of CO converted to products other than $CO_2$. Values for ethanol and acetic acid include quantities present as ethyl esters and as acetates. "Gaseous HC" represents aggregated two-, three-, and four- carbon hydrocarbons. "Total HC" represents Gaseous HC plus $CH_4$, plus any oily, water-insoluble product. "$C_2$ Compounds" represents acetaldehyde plus ethanol, plus acetic acid.
[d] "Rate" is the rate of synthesis of the indicated product in pounds of product per cubic foot of catalyst per hour (lb/cf/hr).

What is claimed is:

1. In a process for the reaction of a synthesis gas containing carbon monoxide and hydrogen in the presence of a hydrogenation catalyst, the improvement for selectively producing two-carbon atom oxygenated hydrocarbon products while minimizing the production of methane which comprises continuously contacting said synthesis gas with a heterogeneous catalyst consisting of rhodium and sodium on a silica gel support at reaction conditions such that product efficiencies based on carbon consumption in excess of 10 percent are achieved and ethanol, acetic acid and acetaldehyde are formed in an amount which is at least about 50 weight percent of the two or more carbon atom compounds produced by the reaction, the concentration of sodium in said catalyst being at least 0.1 weight percent whereby the production of methane is reduced such that the carbon efficiency to methane is lower than the corresponding carbon efficiency when sodium is absent from said heterogeneous catalyst, which reaction conditions include a temperature within the range of from about 150°–450° C., a pressure within the range of from about 15–10,000 psig, and a mole ratio of hydrogen to carbon monoxide within the range of from about 20:1 to 1:200.

2. The process of claim 1 wherein said reaction conditions include a temperature within the range of about 250°–350° C., a pressure within the range of about 300–5,000 psig, and a mole ratio of hydrogen to carbon monoxide within the range of about 5:1 to 1:5.

3. The process of claim 1 wherein the conversion of CO in the synthesis gas is less than about one-fourth, on a single pass basis.

4. The process of claim 1 wherein the space velocity of the synthesis gas is in excess of about $10^3$ GHSV.

5. The process of claim 4 wherein said space velocity is within the range of about $10^4$ to $10^6$ GHSV.

* * * * *